United States Patent [19]

Fliedner, Jr.

[11] 4,343,812

[45] Aug. 10, 1982

[54] ANTIDEPRESSANT 2-AMINO-AND-2-(SUBSTITUTED AMINO)-CIS-HEXAHYDRO-CARBAZOLES, COMPOSITIONS AND USE

[75] Inventor: Leonard J. Fliedner, Jr., Point Lookout, N.Y.

[73] Assignee: E. I. Du Pont de Nemours and Company, Wilmington, Del.

[21] Appl. No.: 155,977

[22] Filed: Jun. 3, 1980

Related U.S. Application Data

[62] Division of Ser. No. 887,779, Mar. 17, 1978, Pat. No. 4,254,134.

[51] Int. Cl.$^3$ .................... A61K 31/40; C07D 209/88
[52] U.S. Cl. ..................................... 424/274; 260/315
[58] Field of Search ......................... 260/315; 424/274

[56] References Cited

U.S. PATENT DOCUMENTS 4,254,134  3/1981  Fliedner ............................... 424/274

OTHER PUBLICATIONS

Grellmann et al., *Chem Abstracts*, vol. 86 (1977) No. 54682E.

*Primary Examiner*—Robert W. Ramsuer

[57] ABSTRACT

2-Amino- and 2-(substituted amino)-tetrahydro- and -cis-hexahydro-carbazoles useful for alleviating depression in mammals or as intermediate compounds thereto.

24 Claims, No Drawings

ANTIDEPRESSANT 2-AMINO-AND-2-(SUBSTITUTED AMINO)-CIS-HEXAHYDRO-CARBAZOLES, COMPOSITIONS AND USE

This is a division of application Ser. No. 887,779, filed Mar. 17, 1978, now U.S. Pat. No. 4,254,134.

BACKGROUND OF THE INVENTION

This invention relates to tetrahydrocarbazoles and cis-hexahydrocarbazoles useful as antidepressant agents and intermediates thereto.

Mooradian in U.S. Pat. No. 3,959,309, discloses analgetic and psychotropic activity for compounds such as

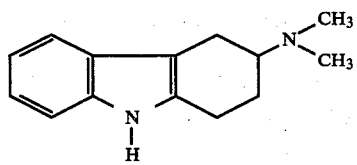

Mooradian et al., [J. Med. Chem. 18, 640 (1975)], discloses that compounds such as

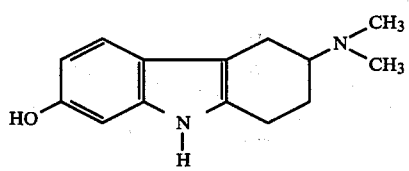

produce cardiotonic effects in dogs.

Canas-Rodriguez, in U.S. Pat. No. 3,720,711 discloses antidepressant activity for compounds such as

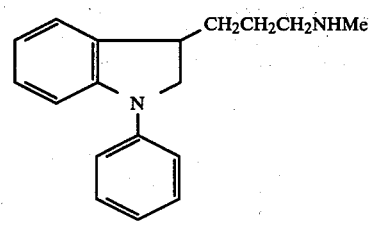

Mental illnesses include psychoses and neuroses. The symptoms requiring treatment include depression, anxiety, agitation and hallucinations. Drugs used particularly for treatment of both reactive and endogenous depressions include monoamine oxidase (MAO) inhibitors such as tranylcypromine, nialamide, phenelzine and pargyline and the non-MAO inhibiting tricyclic aromatic dibenzazepines such as imipramine and dibenzocycloheptenes such as amitriptyline.

All of these drugs have side effects that limit their usefulness. The MAO inhibitors may cause tremors, insomnia, hyperhydrosis, agitation, hypermanic behaviour, confusion, hallucinations, convulsions, orthostatic hypertension and death. They frequently cause dizziness, vertigo, headache, inhibition of ejaculation, difficulty in urination, weakness, fatigue, dry mouth, constipation and blurred vision. Imipramine may cause blurred vision, dryness of mouth, constipation, urinary retention, orthostatic hypotension, respiration depression, myocardial infarction and congestive heart failure. Similar difficulties are experienced with amitriptyline.

The present invention results from efforts to develop new psychotherapeutic compounds which are effective and have minimal side effects. These compounds can be more effective in treating depression than presently available drugs.

SUMMARY OF THE INVENTION

This invention relates to compounds of Formulae I and II and pharmaceutically suitable salts thereof, processes for their manufacture, compositions containing specific compounds of Formulae I and II or their salts, and methods of using specific compounds of Formulae I and II or their salts to alleviate depression in mammals.

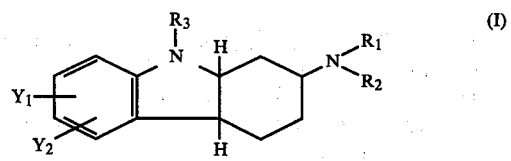

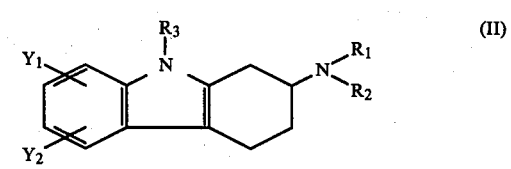

wherein $R_1$ is hydrogen, methyl, ethyl, or

where R is hydrogen, $C_1$-$C_4$ alkyl, methoxy or ethoxy;

$R_2$ is hydrogen or methyl;

$R_3$ is hydrogen, methyl, or ethyl;

$Y_1$ is hydrogen, fluorine, chlorine, bromine, hydroxy, methyl, benzyloxy or $C_1$-$C_6$ alkoxy;

$Y_2$ is hydrogen or chlorine;

with the proviso that $Y_2$ can be chlorine only when $Y_1$ is chlorine.

DETAILED DESCRIPTION OF THE INVENTION

Compounds with Antidepressant Utility

Compounds with antidepressant utility include the compounds of Formula I; also, the compounds of Formula II (referred to as IIa) which have this utility are where:

$R_1$ is hydrogen, methyl, ethyl, or

where R is methyl or ethoxy;

$R_2$ is hydrogen or methyl, provided when $R_1$ is

and R is methyl, then $R_2$ is hydrogen;
$R_3$ is hydrogen, methyl or ethyl;
$Y_1$ is hydrogen, fluorine, chlorine, bromine, methyl, benzyloxy or $C_1$-$C_6$ alkoxy;
$Y_2$ is hydrogen or chlorine;
with the proviso that $Y_2$ can be chlorine only when $Y_1$ is chlorine.

Preferred Compounds

Compounds preferred because of their high degree of antidepressant activity are those compounds of Formula I wherein
$R_1$ is hydrogen, methyl or

where R is $C_1$-$C_4$ alkyl, methoxy or ethoxy; or
$R_2$ is hydrogen; or
$R_3$ is hydrogen, methyl or ethyl; or
$Y_1$ is hydrogen, fluorine, chlorine, bromine or $C_1$-$C_4$ alkoxy; or
$Y_2$ is hydrogen.

Also preferred are those compounds of Formula IIa where
$R_1$ is hydrogen, methyl or

where R is methyl or ethoxy; or
$R_2$ is hydrogen; or
$R_3$ is hydrogen, methyl or ethyl; or
$Y_1$ is hydrogen, fluorine, chlorine, bromine or $C_1$-$C_4$ alkoxy; or
$Y_2$ is hydrogen.

More preferred are those compounds of Formulae I and IIa where $R_1$, $R_2$, $R_3$, and $Y_1$ have the preferred definitions. Most preferred are those compounds of Formulae I and IIa where
$R_1$ is hydrogen, methyl or

where R is $C_1$-$C_4$ alkyl, methoxy or ethoxy, except that in Formula IIa R is limited to methyl or ethoxy;
$R_2$ is hydrogen;
$R_3$ is hydrogen, methyl or ethyl;
$Y_1$ is hydrogen or $C_1$-$C_4$ alkoxy; and
$Y_2$ is hydrogen.

Nomenclature

Formulae I and II encompass tetrahydro- and hexahydro- derivatives of the carbazole ring system

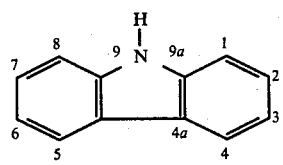

Typical examples of nomenclature for the compounds of the present invention are given as follows:

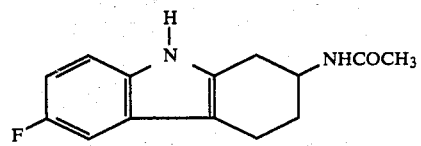

N—(6-fluoro-1,3,4,9-tetrahydro-2H—carbazol-2-yl)acetamide.

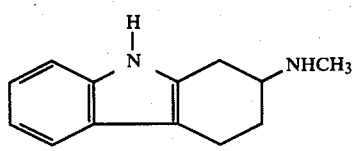

2,3,4,9-Tetrahydro-N—methyl-1H—carbazol-2-amine.

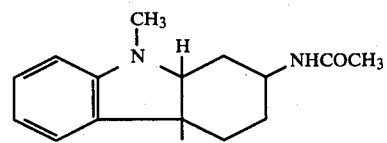

N—(cis-1,3,4,4a,9,9a-hexahydro-9-methyl-2H—carbazol-2-yl)-acetamide.

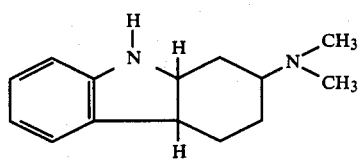

cis-N,N—dimethyl-2,3,4,4a,9,9a-hexahydro-1H—carbazol-2-amine.

Synthesis

Compounds of Formula I are prepared by the reduction of compounds of Formula II wherein $R_1$, $R_2$, $R_3$, $Y_1$, and $Y_2$ are as previously defined.

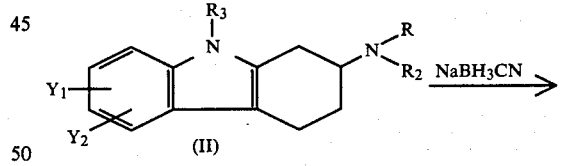

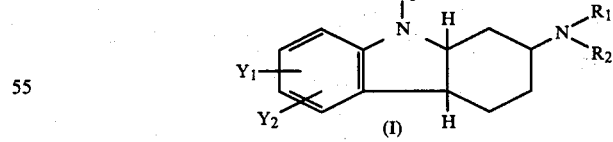

The reduction of tetrahydrocarbazoles to hexahydrocarbazoles is well known in the prior art, e.g., (a) the use of metal-acid mixtures [e.g., tin and hydrochloric acid, cf. B. Robinson, Chem. Rev. 69, 785 (1969)], (b) catalytic hydrogenation in the presence of noble metals and acidic activators [e.g., platinum in ethanolic-aqueous fluoroboric acid, cf. A. Smith, et al., Chem. Commun. 427 (1965)], (c) the use of trimethylamine-borane [cf. J. G. Berger, Synthesis, 508 (1974)], (d) the use of sodium borohydride- or sodium cyanoborohydride-carboxylic acid systems [cf., G. W. Gribble, et al., J. Am. Chem. Soc. 96, 7812 (1974)].

Procedure (d), that of G. W. Gribble, et al., was found to be particularly effective and convenient for the reduction. In this process the compounds of Formula II are dissolved or suspended in a convenient volume of a suitable acidic solvent such as glacial acetic acid, trifluoroacetic acid, or methanolic hydrogen chloride, followed by the addition of sodium cyanoborohydride ($NaBH_3CN$). $NaBH_3CN$ as obtained from commercial sources is usually hygroscopic and although it can be added to the reaction mixture in its solid form, it is, in practice, convenient to dissolve the reagent in an inert solvent in which it is appreciably soluble such as methyl alcohol or ethyl alcohol and then to add the resulting solution to the reaction mixture in a controlled manner. During the addition of the $NaBH_3CN$ (either as a solid or in solution) it is desirable to maintain the internal temperature of the reaction mixture at between 0° C. and 50° C. in order to mitigate the exothermicity and effervescence which accompany said addition. The molar ratio of $NaBH_3CN$ to compound of Formula II is between one and ten. Following the addition of the $NaBH_3CN$, the reaction is brought to completion by stirring the mixture at from ambient temperature to 100° C. for between one and twenty-four hours.

The use of sodium borohydride ($NaBH_4$)-carboxylic acid systems for the alkylation of amines as described by P. Marchini, et al. [J. Org. Chem., 40, 3453 (1975)] provides an effective alternate method for the preparation of compounds of Formula I wherein $R_3$ is methyl, or ethyl, $R_1$ is

where R, $R_2$, $Y_1$ and $Y_2$ are as previously defined. In this process compounds of Formula I with the constituents as defined, except $R_3$ is hydrogen, are alkylated on the nitrogen atom at position 9 by treatment

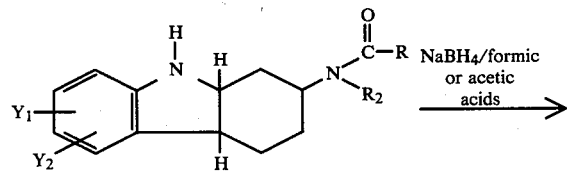

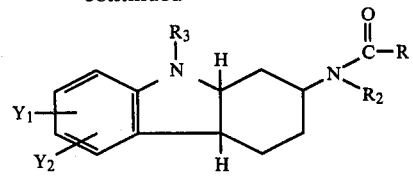

($R_3$ = Me or Et)

with an excess of sodium borohydride and an excess of either formic acid or acetic acid, depending on the alkyl substituent to be introduced, i.e., where $R_3$=methyl (Me) or ethyl (Et), respectively. The reaction is carried out at a temperature of from 20° C. to 100° C. either with or without added inert solvent for a period of from one to twenty-four hours. Suitable inert solvents include benzene and tetrahydrofuran.

With respect to the molecular plane passing through carbon atoms 2, 4a, and 9a of compounds of Formula I, the hydrogen atom at position 4a may be spatially oriented on the same side (cis-relationship) or on the opposite side (trans-relationship) of the plane as the hydrogen atom at position 9a. The hexahydrocarbazoles of Formula I produced by the reduction of compounds of Formula II are cis-isomers, that is the hydrogen atoms at positions 4a and 9a are spatially oriented on the same side of the molecular plane passing through carbon atoms 2, 4a, and 9a.

Each of the cis- compounds of Formula I exist in two diastereoisomeric forms by virtue of the asymmetric carbon atom at position 2, and the invention includes the compounds as the separate diastereoisomers, as well as mixtures thereof, as produced by the above methods. The diastereoisomeric forms in turn can be resolved into optically-active dextrorotatory (+) and levorotatory (−) enantiomers by methods known in the art. All of these optical isomers are included within the scope of the invention since they have utility in alleviating depression in mammals.

The compounds of Formula II which serve as useful intermediates for the synthesis of compounds of Formula I and which also, in many cases, possess antidepressant activity themselves, are prepared by the process known in the art as the Fischer Indole Synthesis. Thus, they are obtained by reacting an appropriate phenylhydrazine of Formula III, wherein $R_3$, $Y_1$ and $Y_2$ are as defined in Formula I, with a cyclohexanone derivative of Formula IV, wherein $R_1$ and $R_2$ are as defined in Formula I, in an acidic medium, at elevated temperatures, for from about ½ hour to 24 hours. The acid cyclizing agent can be an inorganic hydrohalide such as hydrochloric acid or hydrobromic acid or a mineral acid such as phosphoric acid or sulfuric acid, an organic acid such as acetic acid or methanesulfonic acid or a Lewis acid such as boron trifluoride or zinc chloride. The acidic agent should be present in at least one mole in

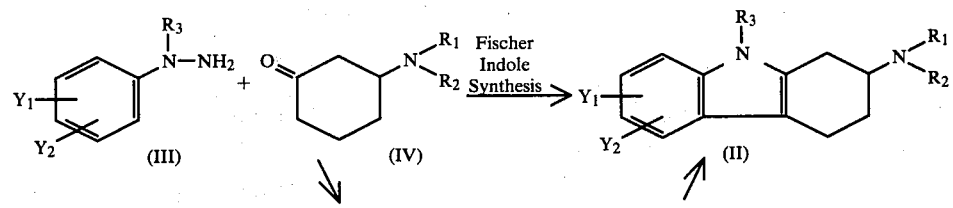

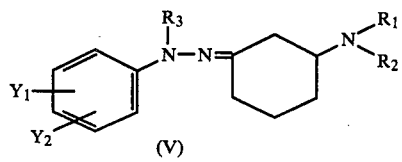

excess per mole of the phenylhydrazine. The reaction is conveniently carried out by heating the reactants in acetic acid at from 80° C. to 120° C. or in ethanolic hydrogen chloride at reflux temperature. The reaction proceeds via the corresponding phenylhydrazone precursor (V) which can be isolated, if desired, by using only a catalytic amount of acid. Subsequent treatment of the phenylhydrazone precursor (V) under acidic conditions, as described above, will effect cyclization to the corresponding tetrahydrocarbazoles of Formula II.

The starting materials III and IV are either commercially available, known to the art, or readily preparable by conventional means.

All of the tetrahydrocarbazoles of Formula II need not be prepared directly via the Fischer indole reaction. Instead interconversions among these compounds are possible in which one tetrahydrocarbazole of Formula II serves as a precursor for another tetrahydrocarbazole of Formula II. Such transformations are effected by conventional means and include the following:

(1) Dealkylation of phenolic ethers of Formula IX, wherein R, R$_2$, and R$_3$ are as defined in Formula II, and R$_4$ is a methyl or benzyl group, may be carried out by means of

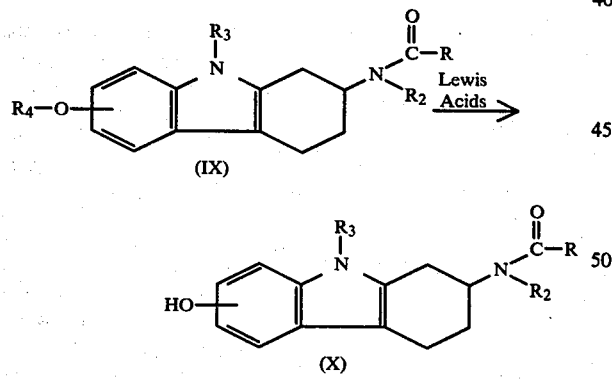

Lewis acids under appropriate conditions [cf. E. Haslam, "Protective Groups in Organic Chemistry", J. F. W. McOmie, Ed., Plenum Press, New York, N.Y., 1973, pp. 164–167]. Alternatively, hydrogenolytic conditions may be effectively employed in cleaving benzyl phenolic ethers of Formula IX (i.e., R$_4$=C$_6$H$_5$CH$_2$) [cf., Idem., ibid., p. 168].

(2) The phenolic tetrahydrocarbazoles of Formula X, wherein R, R$_2$, and R$_3$ are as defined in Formula II, may, in turn, be O-alkylated by reaction with an alkyl halide, or alkyl sulfate, or alkyl sulfonate, in the presence of a base and a suitable inert solvent [cf., Idem., ibid., p. 149]. The resulting

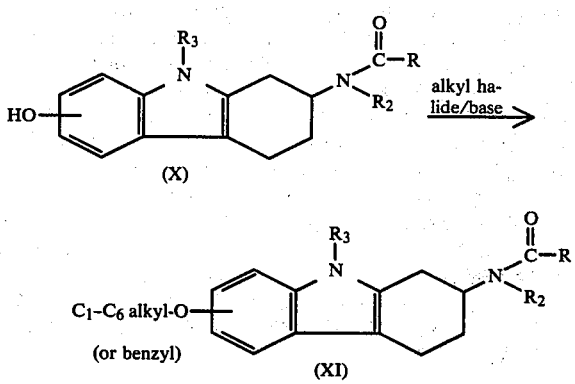

alkoxy tetrahydrocarbazoles of Formula XI, wherein R, R$_2$, and R$_3$ are as defined in Formula II, are isolated by conventional techniques.

(3) Hydrolysis of compounds of Formula XII, wherein R, R$_2$, R$_3$, Y$_1$ and Y$_2$ are as defined in Formula II, with standard acidic or basic reagents such as aqueous hydrochloric acid

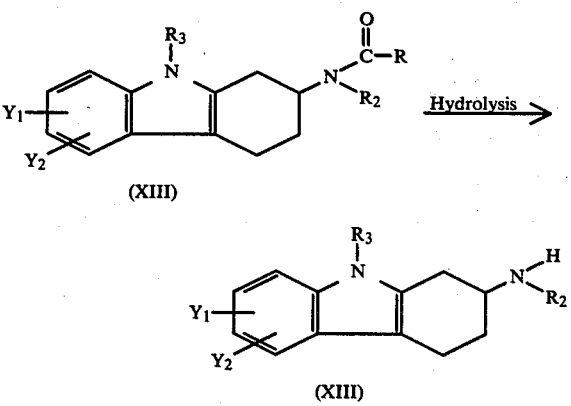

or aqueous-alcoholic sodium hydroxide at reflux temperature provides the amino tetrahydrocarbazoles of Formula XIII wherein R$_2$, R$_3$, Y$_1$ and Y$_2$ are as defined in Formula II [cf., J. W. Barton, ibid., pp. 46–50].

(4) Acyl and urethane-type tetrahydrocarbazoles of Formula XIII, wherein R, R$_2$, R$_3$, Y$_1$ and Y$_2$ are as defined previously, are obtained by reacting a compound of Formula XIII, wherein R$_2$, R$_3$, Y$_1$ and Y$_2$ are as defined previously, with an acylating agent [cf., Idem., ibid, pp. 46–50]. In those cases where acidic

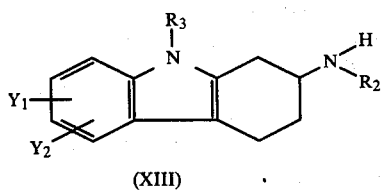

(XIII)

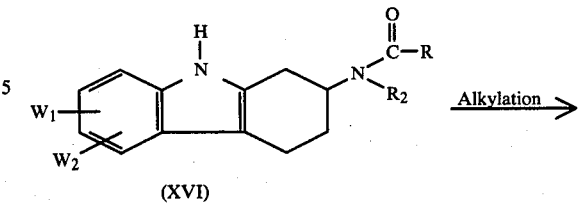

(XVI)

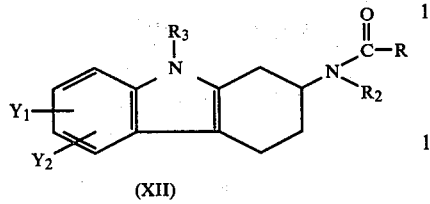

(XII)

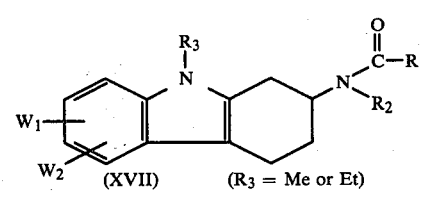

(XVII)  (R₃ = Me or Et)

by-products occur, such as hydrogen chloride, the acylation reaction can be conducted in the presence of a standard basic reagent such as sodium hydrogen carbonate or triethylamine. The basic reagents neutralize the acidic by-products which otherwise may have a deleterious effect on the course of the reaction. Suitable acylating agents include formamide, acetyl chloride, acetic anhydride, methyl or ethyl chloroformate, propanoyl chloride, butanoyl chloride, and pentanoyl chloride. Suitable inert solvents for carrying out the acylation reaction include benzene, ether, chloroform, or methylene chloride, or a mixture of one of these solvents with water to produce a two-phase system.

(5) Reduction of amido tetrahydrocarbazoles of Formula XIV, wherein $R_2$, $R_3$, $Y_1$, and $Y_2$ are defined as in Formula II and $R_5$ is selected from the group consisting of hydrogen, methyl, $OCH_3$, or $OC_2H_5$, is effected by adding the substrate either to a solution or suspension of lithium aluminum hydride (LAH) in anhydrous ethyl ether or anhydrous tetrahydrofuran (THF) or mixtures thereof or to a solution of sodium bis(2-methoxyethoxy) aluminum hydride in benzene and refluxing the resulting solutions for a period of from one to twenty-four hours. Conventional work-up procedures yield the amino tetrahydrocarbazoles of Formula XV, wherein $R_2$, $R_3$, $Y_1$ and $Y_2$ are defined as in Formula II and $R_6$ is selected from

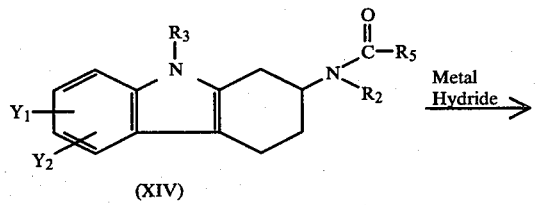

(XIV)

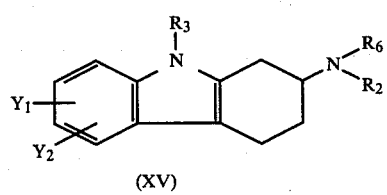

(XV)

methyl or ethyl.

(6) Compounds of Formula XVI wherein R and $R_2$ are defined as in Formula II, and $W_1$ is a hydrogen, a fluorine, a chlorine, a bromine atom, or a methyl, a benzyloxy, or a $C_1$-$C_6$ alkoxy group and $W_2$ is a hydrogen or chlorine atom with the proviso that $W_2$ can be chlorine only when $W_1$ is chlorine, may be alkylated at the $N^9$-position to yield compounds of Formula XVII, wherein R and $R_2$ are defined as in Formula II, $W_1$ and $W_2$ are defined as in Formula XVI and $R_3$ is methyl or ethyl. The literature [cf. H. Heaney, et al., J. Chem. Soc. Perkin 1, 499 (1973) and references therein] teaches a number of methods for obtaining N-alkyl-indoles and N-alkyl-pyrroles from the corresponding unalkylated compounds in satisfactory yields.

Generally, the alkylation process involves reaction of the unalkylated substrate with a basic reagent sufficiently strong to form an anion at the nitrogen atom. Nucleophilic attack of this anion on the subsequently added alkylating agent then completes the reaction.

As applied to the tetrahydrocarbazoles of Formula XVI, the procedure of H. Heaney, et al. (loc. cit.) was found to be particularly effective for obtaining $N^9$-alkylated tetrahydrocarbazoles of Formula XVII. Thus, mixing of a compound of Formula XVI with a solution of potassium hydroxide in dimethyl sulfoxide (DMSO) formed the $N^9$-anion of the compound of Formula XVI which on subsequent treatment with methyl iodide or ethyl iodide formed the desired products of Formula XVII, wherein $R_3$ is methyl or ethyl, respectively.

The compounds of Formula II exist in dextroratatory [(+)-] and levorotatory [(-)-] optically active isomeric forms, by virtue of the asymmetric carbon atom at position 2 and the invention includes the compounds in the separated [(+)-] and [(-)-] forms, as well as the racemic [(±)-] mixtures produced by the above methods. Compounds of Formulae I and II can be converted to acid addition salts. Thus appropriate compounds of Formulae I and II form pharmaceutically acceptable addition salts with, for example, both pharmaceutically acceptable organic and inorganic acids, such as acetic acid, citric acid, maleic acid, methanesulfonic acid, succinic acid, tartaric acid, hydrochloric acid, nitric acid, phosphoric acid, sulfuric acid, and the like. Nonpharmaceutically acceptable acid addition salts of appropriate compounds of Formulae I and II may be useful in purification and isolation procedures and can be converted into pharmaceutically acceptable acid addition salts via conventional metathetic reactions whereby the nonpharmaceutically acceptable anion is replaced by a pharmaceutically acceptable anion; or alternatively, by neutralizing the nonpharmaceutically acceptable acid addition salt and then reacting the soobtained free base with a reagent yielding a pharmaceutically acceptable acid addition salt.

Where the compounds of Formulae I and II contain one basic center, mono addition salts can be obtained by general procedures known to the art. Where the compounds of Formula I contain two basic centers, mono- or di-addition salts can be obtained by general procedures known to the art depending on the relative basicity of such centers and the relative quantities of the reactants and reaction conditions employed in preparing such salts.

Dosage Forms

The antidepressant agents of this invention can be administered as treatment for psychiatric depressions of the reactive and endogenous types by any means that produces contact of the active agent with the agent's site of action in the body of a mammal. They can be administered by any conventional means available for use in conjunction with pharmaceuticals; either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired.

The compounds of this invention will have a therapeutic dose range in man from 0.1 to 50 mg/kg/day; some of the more preferred compounds will have a dose range from 0.5 to 10 mg/kg/day and the most preferred dose range will be from 1 to 5 mg/kg/day.

Dosage forms (compositions) suitable for internal administration contain from about 2.5 milligrams to about 250 milligrams of active ingredient per unit. In these pharmaceutical compositions the active ingredient will ordinarily be present in an amount of about 0.01–90% by weight based on the total weight of the composition.

The active ingredient can be administered orally in solid dosage forms, such as capsules, tablets, and powders, or in liquid dosage forms, such as elixers, syrups, and suspensions, it can also be administered parenterally, in sterile liquid dosage forms; or rectally in the form of suppositories.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA (ethylenediaminetetraacetic acid). In addition, parenteral solutions can contain preservatives, such as benzalkonium chloride, methyl- or propyl-paraben, and chlorobutanol.

Suppositories contain the active ingredient in a suitable oleaginous or water-soluble base. The oleaginous class includes cocoa butter and fats with similar properties; the water-soluble class includes polyethylene glycols.

Suitable pharmaceutical carriers are described in *Remington's Pharmaceutical Sciences,* E. W. Martin, a standard reference text in this field.

Useful pharmaceutical dosage-forms for administration of the compounds of this invention can be illustrated as follows:

Capsules

Capsules can be prepared by filling standard two-piece hard gelatin capsules with the following mixture using conventional encapsulating equipment:

| | |
|---|---|
| Active ingredient | 37.5 mg |
| Lactose | 150 mg |
| Talc | 15 mg |
| Magnesium stearate | 7.5 mg |

Capsules

A mixture of active drug in soy bean oil is prepared and injected by means of a positive displacement pump in gelatin to form soft gelatin capsules containing 37.5 mg of the active ingredient. The capsules are washed in petroleum ether and dried.

Tablets

Tablets can be prepared by conventional procedures so that each unit will contain:

| | |
|---|---|
| Active ingredient | 37.5 mg |
| Spray dried lactose | 200 mg |
| Polyvinyl pyrrolidone | 2 mg |
| Microcrystalline cellulose | 30 mg |
| Magnesium stearate | 4 mg |

Parenteral

A parenteral composition suitable for intra muscular administration is prepared so that each ml contains:

| | |
|---|---|
| Active ingredient | 37.5 mg |
| Polysorbate 80 | 1 mg |
| Sodium chloride | 0.9% |
| Methylparaben | 1 mg |
| Propylparaben | 0.1 mg |
| Water for Injection Q.S. | 1.0 ml |

Suspension

An aqueous suspension is prepared for oral administration so that each 5 mls contain:

| | |
|---|---|
| Active ingredient | 37.5 mg |
| Methylcellulose | 5% |
| Carboxy methyl cellulose | 5% |
| Syrup | 30% |
| Sorbitol | 15% |
| Sodium Saccharin | 2 mg |
| Butterscotch Flavor | 0.2% |
| Sodium Benzoate | 5 mg |
| Water Q.S. | 5 ml |

Use

A standard procedure for detecting and comparing the antidepressant activity of compounds in this series for which there is good correlation with human efficacy is the prevention of tetrabenazine-induced sedation and depression in mice. (Everett, "The Dopa Response Potentiation Test and Its Use in Screening for Antidepressant Drugs", pp. 164–167 in "Antidepressant Drugs" [Proceedings of the First International Symposium], S. Garattini and M. N. G. Dukes, eds., 1967).

Groups of 10 Carworth $CF_1S$ female mice, 18–21 g each, were fasted 1.5 hours and were intubated with antagonist compounds at oral doses of 0, 5, 25, and 125 mg/kg or 0, 1, 3, 9, 27, and 81 mg/kg in 0.20 ml of 1% Methocel (methylcellulose). The mice were challenged 30 minutes later with tetrabenazine (as the methane-sulfonate), 32 mg/kg intraperitoneally (dissolved in 0.20 ml 0.05 M KCl at pH 2.0). One hour after antagonist (30 minutes after tetrabenazine), the mice were examined for signs of exploratory activity and ptosis (eyelid closure). Normal exploratory activity (relief from sedation) was recorded when a mouse lifted by the tail from a group of 10 in a testing box and placed on a stainless steel testing box lid (12.5"×8" with 0.33" mesh) either turned its head horizontally 30° in both directions or moved to the edge of the screen within 10 seconds after being placed on the screen. Relief from ptosis was recorded when exactly two seconds after placing the mouse facing the observer, lid closure was less than 50% in both eyes.

For comparison, the marketed antidepressant amitriptylene was also tested, and an $ED_{50}$ (effective dose in 50% of the cases) was determined. The lower the $ED_{50}$, the better the antidepressant. Results for compounds of this invention are tabulated in Table IV.

The following examples will more fully illustrate the preparation of the compositions of the invention. All temperatures in the examples are given in degrees Centigrade.

EXAMPLE 1 (Table I)

N-(cis-1,3,4,4a,9,9a-hexahydro-2H-carbazol-2-yl)acetamide hydrochloride (Compound 1a)

A solution of 5.70 g (0.025 mol) of N-(1,3,4,9-tetrahydro-2H-carbazol-2-yl)acetamide in 140 ml of glacial HOAc was stirred at room temperature, and, during the course of 5–10 minutes, a solution of 1.57 g (0.025 mol) of $NaBH_3CN$ in 15 ml of MeOH was added dropwise. The reaction was mildly exothermic with gentle effervescence. After stirring overnight (ca. 16 hr) at room temperature, the glacial HOAc was evaporated and the residue mixed with 150 ml of $H_2O$. Conc. HCl was added dropwise (pH 1–2), and, after stirring for 0.5–1 hr, any insolubles were removed by filtration. The clear, colorless filtrate was made basic with excess 50% NaOH, and the product was extracted with $CHCl_3$. The extracts were washed with $H_2O$, dried, evaporated, and the residue recrystallized from i-PrOH to give 3.64 g (70% yield) of white solid, mp 190°–191°.

A solution of the free base in methanol was treated with an excess of hydrogen chloride. Addition of anhydrous ether precipitated the title compound, which, after cooling, was filtered and recrystallized, mp 245°–247°.

In an analogous manner, utilizing the procedure of Example 1, the compounds in Table I were prepared. In the preparation (0.025 mole scale) of 1 g, the glacial HOAc was evaporated and the residue treated with 60 ml of $H_2O$. On addition of concentrated HCl to pH 1–2, the hydrochloride salt precipitated directly from the initially clear solution and was isolated by filtration. The ten-fold molar amount of $NaBH_3CN$ used for the preparation 1×(Table 1) was divided into two equal portions and added 7 hr apart. Stirring was then continued overnight at room temperature.

The compounds described in Table I were characterized and tested for biological activity either as the free bases or their hydrochloride salts (see Formula Column).

EXAMPLE 2 (Table I)

N-(cis-9-ethyl-1,3,4,4a,9,9a-hexahydro-2H-carbazol-2-yl) acetamide (Compound 1y)

A solution of 9.0 g (0.15 mol) of glacial acetic acid in 75 ml of THF was treated in portions with 1.89 g (0.05 mol) of $NaBH_4$, the temperature being kept at 20° C. When the evolution of $H_2$ had ceased (ca. 3 hr), 2.30 g (0.01 mol) of N-(cis-1,3,4,4a,9,9a-hexahydro-2H-carbazol-2-yl)acetamide was added and the resulting solution was refluxed for 3 hr. After cooling, the THF was evaporated in vacuo and the residue was dissolved in $CHCl_3$. The $CHCl_3$ solution was washed with 1 N aq NaOH and then dried over anhydrous $K_2CO_3$. Filtration followed by evaporation of the $CHCl_3$ left a white solid residue which after recrystallization from ethyl acetate-cyclohexane yielded 2.3 g of the title compound, mp 150°–151°.

By substituting formic acid for acetic acid and otherwise utilizing the procedure of Example 2, N -(cis-1,3,4,4a,9,9a-hexahydro-9-methyl-2H-carbazol-2-yl)acetamide (Compound 1o, Table I) can be prepared from N-(cis-1,3,4,4a,9,9a-hexahydro-2H-carbazol-2-yl)acetamide.

EXAMPLE 3 (Table II)

N-(1,3,4,9-tetrahydro-2H-carbazol-2-yl)acetamide (Compound 2a)

A stirred solution of 140.9 g (0.909 mol) of N-(3-oxocyclohexyl)acetamide in 900 ml of glacial HOAc was heated at 85°–95° C. while 98.2 g (0.909 mol) of phenylhydrazine was added dropwise during 1 hr. After an additional 3 hr at 95°±5°, the hot solution was poured into 5 l. of $H_2O$. When the initially formed gum had solidified, the product was filtered, washed with 2.5 l. of $H_2O$, then 2 l. of $Et_2O$ to give 167.6 g (81%) of a grey solid, mp 203°–206°. Recrystallization was best effected by dissolving the crude solid in boiling $Me_2CO$ (1 g/25 ml) and boiling down to 1 g/10 ml. The resulting yellow solid (133.5 g, mp 208°–209°) was recrystallized again from $Me_2CO$ to yield 111.8 g of white solid, mp 208°–209°. To remove $Me_2CO$ occluded by the crystalline solid, the product was further recrystallized

EXAMPLE 4 (Table II)

N-(6-fluoro-1,3,4,9-tetrahydro-2H-carbazol-2-yl)acetamide (Compound 2b)

A mixture of 0.05 mol of 4-fluorophenylhydrazine hydrochloride and 0.05 mol of N-(3-oxocyclohexyl)acetamide in 75 ml of glacial HOAc was stirred and heated on the steam bath. At 80°–90° an exothermic reaction occurred and the source of heat was removed until the temperature had fallen to 85°. After an additional 4–5 hr at 85°–90°, the warm mixture was poured into $H_2O$ and the gummy insolubles triturated until solid. The filtered solid was washed thoroughly with $H_2O$ and then with $Et_2O$ until the washings were essentially colorless. The crude product was recrystallized from ethanol to give the title compound, mp 209°–210°.

By substituting 4-chlorophenylhydrazine hydrochloride, 2-fluorophenylhydrazine hydrochloride, or 3,5-dichlorophenylhydrazine hydrochloride for 4-fluorophenylhydrazine hydrochloride and otherwise utilizing the procedure of Example 4, compounds 2c, 2e, and 2f (Table II), respectively, were prepared.

EXAMPLE 5 (Table II)

N-(6-bromo-1,3,4,9-tetrahydro-2H-carbazol-2-yl)acetamide (Compound 2d)

A solution of 0.05 mol of N-(3-oxocyclohexyl)acetamide in 100 ml of glacial HOAc was stirred and heated at 80° C. while adding during 15–30 minutes a warm solution of 0.05 mol of 4-bromophenylhydrazine hydrochloride in 300 ml of glacial HOAc. After an additional 3 hr at 85°, most of the HOAc was evaporated. The residue was triturated with $H_2O$, until solid, the resulting solid was filtered, and recrystallized from ethanol to give the title compound, mp 210°–211°.

By substituting 4-methylphenylhydrazine hydrochloride for 4-bromophenylhydrazine hydrochloride and otherwise utilizing the procedure of Example 5, compound 2g (Table II) was prepared.

EXAMPLE 6 (Table II)

N-(1,3,4,9-tetrahydro-6-methoxy-2H-carbazol-2-yl)acetamide (Compound 2h)

A mixture of 0.05 mol of N-(3-oxocyclohexyl)acetamide, 0.05 mol of anhydrous NaOAc, 0.05 mol of 4-methoxyphenylhydrazine hydrochloride, and 155 ml of glacial HOAc was stirred for 1 hr at room temperature and then refluxed for 1 hr. The cooled reaction mixture was poured into $H_2O$ and the product triturated until solid. Filtration, drying, and recrystallization from ethanol gave the title compound, mp 191°–193°.

EXAMPLE 7 (Table II)

N-(1,3,4,9-tetrahydro-7-methoxy-2H-carbazol-2-yl)acetamide (Compound 2i)

A mixture of 0.05 mol of N-(3-oxocyclohexyl)acetamide and 0.05 mol of 3-methoxyphenylhydrazine hydrochloride in 50 ml of glacial HOAc was stirred for 2 hr at room temperature and then refluxed for 2 hr. The cooled reaction mixture was poured into $H_2O$ and the product triturated until solid. Filtration, drying, and recrystallization from ethanol gave the title compound, mp 192°–193°.

from EtOH, 86% recovery of white solid, mp 208°–209°.

EXAMPLE 8 (Table II)

N-(7-n-butyloxy-1,3,4,9-tetrahydro-2H-carbazol-2-yl)acetamide (Compound 2j)

A mixture of 0.2 mol of 3-n-butyloxyphenylhydrazine, 0.2 mol of N-(3-oxocyclohexyl)acetamide, and 350 ml of glacial HOAc was stirred at room temperature for 3 hr and then refluxed for 2 hr. After pouring into 2.5 l of $H_2O$ and stirring overnight, the insoluble material had partly crystallized. The crystalline material was filtered, washed with $H_2O$, and dried (23 g, Fraction A). The remaining insoluble semi-solid was taken up in EtOAc, washed with $H_2O$, dried, and evaporated. The dark residue was triturated with $Et_2O$ and filtered (6.7 g, mp 181°–183°, Fraction B). Additional product was extracted from Fraction A by stirring with two 4 l. portions of $Et_2O$. The combined extracts were evaporated and the resulting residue combined with Fraction B and recrystallized twice from $Me_2CO$ to yield 10.2 g of the title compound, mp 182°–184°.

EXAMPLE 9 (Table II)

N-(1,3,4,9-tetrahydro-7-hydroxy-2H-carbazol-2-yl)acetamide (Compound 2k)

A solution of 25.8 g (0.1 mol) of N-(1,3,4,9-tetrahydro-7-methoxy-2H-carbazol-2-yl)acetamide in 2 l. of $CH_2Cl_2$ was stirred at −50° to −60° C. under $N_2$ while adding 101 g (0.4 mol) of $BBr_3$ dropwise during 15–30 min. Stirring was continued for 30 min at −55° C. and then 3 hr at room temperature. After cooling to −40° C., 600 ml of MeOH was cautiously added dropwise during 45 min. The reaction mixture was allowed to warm to room temperature (ca. 1 hr) and then evaporated. The residue was dissolved in one l. of 1 N KOH, filtered from insolubles, and the cold filtrate was acidified (pH 3) with conc. HCl. The precipitate was filtered, washed with $H_2O$, and recrystallized from i-PrOH to give the title compound, mp 245°–246°.

EXAMPLE 10 (Table II)

N-(7-ethoxy-1,3,4,9-tetrahydro-2H-carbazol-2-yl)acetamide (Compound 2L)

A mixture of 0.02 mol of N-(1,3,4,9-tetrahydro-7-hydroxy-2H-carbazol-2-yl)acetamide, 0.022 mol of ethyl iodide, 0.022 mol of anhydrous $K_2CO_3$, and 50 ml of $Me_2CO$ was stirred and refluxed for 48 hr. Sufficient $CHCl_3$ and $H_2O$ were added to the cooled reaction mixture to give two clear layers. The $CHCl_3$ layer was washed with 1 N NaOH, $H_2O$, dried, evaporated, and the resulting solid residue was recrystallized from i-PrOH to give the title compound, mp 184°–186°.

By substituting n-propyl iodide, n-pentyl bromide, n-hexyl bromide, or benzyl bromide for ethyl iodide and otherwise utilizing the procedure of Example 10, compounds 2m, 2n, 2o, and 2p (Table II), respectively, were prepared.

EXAMPLE 11 (Table III)

2,3,4,9-Tetrahydro-1H-carbazol-2-amine hydrochloride (Compound 3a)

A mixture of 139.3 g (0.611 mol) of N-(1,3,4,9-tetrahydro-2H-carbazol-2-yl)acetamide, 402.6 g of powdered KOH, and 2 l. of n-BuOH was stirred and refluxed under $N_2$ for 16 hr. The reaction mixture was cooled to room temperature, diluted with 2.4 l. of $H_2O$, and stirred for 1 hr. The upper organic layer was separated and evaporated while the aqueous phase was extracted with CHCl₃ (3×750 ml). The extracts were combined with the solid evaporation residue and the resulting solution washed with H₂O (3×750 ml) and dried. The granular solid remaining after evaporation of the CHCl₃ was triturated with 750 ml of Et₂O. The bulk of the product was allowed to settle and the Et₂O phase, which contained a small amount of amorphous insolubles, was decanted. This process was repeated with one-half the quantity of Et₂O. Finally, the product was collected by filtration and dried to give 99.1 g of a light cream-tan solid, mp 151°–153°.

A solution of the free base in methanol was treated with an excess of hydrogen chloride. Addition of anhydrous ether precipitated the title compound, which, after cooling, was filtered and recrystallized, mp ca. 290° dec.

EXAMPLE 12 (Table III)

N-(1,3,4,9-tetrahydro-2H-carbazol-2-yl)formamide (Compound 3b)

A mixture of 8.90 g (0.048 mol) of 2,3,4,9-tetrahydro-1H-carbazol-2-amine and 65 ml of dry formamide was stirred and heated under N₂ for 5 hr at 95°–100° C. The cooled reaction mixture was poured into H₂O, and the precipitated gum extracted with CHCl₃. The combined extracts were washed with 0.1 N HCl, 5% aqueous NaHCO₃, and H₂O, and dried. Et₂O-trituration of the residue remaining after evaporation of the CHCl₃ gave a tan solid, 8.58 g, mp 123°–126°. For analysis, it was necessary to dry the recrystallized (EtOH) sample at 120° (P₂O₅, 0.02 mm, 20 hr), mp 169°–171°.

EXAMPLE 13 (Table III)

N-(1,3,4,9-tetrahydro-2H-carbazol-2-yl)propanamide (Compound 3c)

A solution of 0.05 mol of 2,3,4,9-tetrahydro-1H-carbazol-2-amine in 450 ml of CHCl₃ and 185 ml of saturated aqueous NaHCO₃ was stirred vigorously at room temperature and treated dropwise during 30 min with a solution of 0.15 mol of propanoyl chloride in an equal volume of CHCl₃. After stirring vigorously for 5 hr, the CHCl₃ layer was separated, washed in succession with 10% aqueous K₂CO₃, H₂O, 0.1 N hydrochloric acid, H₂O, and dried over anhydrous Na₂SO₄. The residue remaining after evaporation of the CHCl₃ was recrystallized from ethyl acetate to give the title compound, mp 169°–170°.

By substituting pentanoyl chloride, ethyl chloroformate, or methyl chloroformate for propanoyl chloride and otherwise utilizing the procedure of Example 13, compounds 3d, 3e, and 3f (Table III), respectively, were prepared.

EXAMPLE 14 (Table III)

Methyl(1,3,4,9-tetrahydro-2H-carbazol-2-yl)carbamic acid, ethyl ester (Compound 3g)

A solution of 0.05 mol of 2,3,4,9-tetrahydro-N-methyl-1H-carbazol-2-amine in 450 ml of CH₂Cl₂ and 185 ml of saturated aqueous NaHCO₃ was stirred vigorously at room temperature and treated dropwise during 30 min with a solution of 0.15 mol of ethyl chloroformate in an equal volume of CH₂Cl₂. After stirring vigorously for 5 hr, the CH₂Cl₂ layer was separated, washed in succession with 10% aqueous K₂CO₃, H₂O, 0.1 N hydrochloric acid, H₂O, and dried over anhydrous Na₂SO₄. The residue remaining after evaporation of the CH₂Cl₂ was recrystallized from ethanol to give the title compound, mp 167°–168°.

EXAMPLE 15 (Table III)

N-(1,3,4,9-tetrahydro-2H-carbazol-2-yl)-N-methylacetamide (Compound 3h)

A mixture of 10.0 g (0.05 mol) of 2,3,4,9-tetrahydro-N-methyl-1H-carbazol-2-amine and 70 ml of acetic anhydride was heated at reflux until complete solution occurred (2–3 min). After standing overnight at room temperature and further cooling at 0°, the precipitated solid was filtered, washed first with small portions of cold acetic anhydride and then thoroughly with anhydrous ether. The crude product was recrystallized from ethanol to give the title compound, mp 215°–216°.

EXAMPLE 16 (Table III)

N-ethyl-2,3,4,9-tetrahydro-1H-carbazol-2-amine hydrochloride (Compound 3i)

A solution of 22.8 g (0.1 mol) of N-(1,3,4,9-tetrahydro-2H-carbazol-2-yl)acetamide in 500 ml of anhydrous THF was added dropwise during 1 hr to a stirred suspension of 18.95 g (0.5 mol) of LiAlH₄ in 400 ml of anhydrous THF. The reaction was carried out in a nitrogen atmosphere. After refluxing for 36 hr, the cold reaction mixture was carefully decomposed with aqueous NaOH. The inorganic salts which precipitated were filtered, washed with THF, and the combined filtrate and washings were evaporated in vacuo to dryness. The residue was recrystallized twice from isopropanol to give the free base of the title compound, mp 170°–172°.

A warm solution of the free base in methanol was treated with excess 10% methanolic hydrogen chloride. A precipitate readily formed, which, after cooling, was filtered and recrystallized to yield the title compound, mp 263°–264°.

EXAMPLE 17 (Table III)

2,3,4,9-Tetrahydro-N-methyl-1H-carbazol-2-amine hydrochloride (Compound 3j)

A solution of 25.8 g (0.1 mol) of (1,3,4,9-tetrahydro-2H-carbazol-2-yl)carbamic acid, ethyl ester in 150 ml of anhydrous THF was added dropwise during 1 hr to a stirred suspension of 15.2 g (0.4 mol) of LiAlH₄ in a mixture of 375 ml of anhydrous ether and 375 ml of anhydrous THF. The reaction was carried out in a nitrogen atmosphere. After refluxing for 16 hr, the cold reaction mixture was carefully decomposed with aqueous NaOH. The inorganic salts which precipitated were filtered, washed with THF, and the combined filtrate and washings were evaporated in vacuo to dryness. The residue was recrystallized twice from isopropanol to give the free base of the title compound, mp 139°–140°.

A warm solution of the free base in ethanol was treated with excess 10% ethanolic hydrogen chloride. A precipitate readily formed which, after cooling, was filtered and recrystallized to yield the title compound, mp 252°–253°.

By substituting methyl(1,3,4,9-tetrahydro-2H-carbazol-2-yl)carbamic acid, ethyl ester for (1,3,4,9-tetrahydro-2H-carbazol-2-yl)carbamic acid, ethyl ester and otherwise utilizing the procedure of Example 17, compound 3k (Table III) was prepared.

EXAMPLE 18 (Table III)

N-(1,3,4,9-tetrahydro-9-methyl-2H-carbazol-2-yl)acetamide (Compound 3L)

A mixture of 0.1 mol of N-(1,3,4,9-tetrahydro-2H-carbazol-2-yl)acetamide, 0.15 mol of powdered KOH, and 75 ml of DMSO was stirred under nitrogen for 2 hr at room temperature. Methyl iodide (0.15 moL) was added in one portion, and, after brief cooling to moderate the exothermic reaction, the mixture was stirred at room temperature for 2 hr. The precipitate obtained by pouring the reaction mixture into excess water, was filtered, washed with water, and recrystallized from ethyl acetate to give the title compound, mp 171°–172°.

TABLE I

| No. | $Y_1$ | $Y_2$ | $R_1$ | $R_2$ | $R_3$ | Example 1 Mol Ratio[a] | Recrystn Solvent | Mp, °C. | Formula |
|---|---|---|---|---|---|---|---|---|---|
| 1a | H | H | COMe | H | H | 1 | EtOH | 245–247 | $C_{14}H_{18}N_2O \cdot HCl$ |
| 1b | 6-F | H | COMe | H | H | 2 | i-PrOH | 242–244 | $C_{14}H_{17}FN_2O \cdot HCl$ |
| 1c | 6-Cl | H | COMe | H | H | 1.5 | MeOH | 253–254 | $C_{14}H_{17}ClN_2O \cdot HCl$ |
| 1d | 6-Br | H | COMe | H | H | 1 | 95% EtOH | 243–244 | $C_{14}H_{17}BrN_2O \cdot HCl$ |
| 1e | 6-Me | H | COMe | H | H | 1 | EtOH | 232–233 | $C_{15}H_{20}N_2O \cdot HCl$ |
| 1f | 6-MeO | H | COMe | H | H | 1 | 95% EtOH | 240–241 | $C_{15}H_{20}N_2O_2 \cdot HCl$ |
| 1g | 7-HO | H | COMe | H | H | 1 | EtOH—H$_2$O | 284–285 | $C_{14}H_{18}N_2O_2 \cdot HCl$ |
| 1h | 7-MeO | H | COMe | H | H | 1 | H$_2$O | 253–254 | $C_{15}H_{20}N_2O_2 \cdot HCl$ |
| 1i | 7-EtO | H | COMe | H | H | 1 | i-PrOH | 196–198 | $C_{16}H_{22}N_2O_2$ |
| 1j | 7-n-PrO | H | COMe | H | H | 1 | i-PrOH | 190–192 | $C_{17}H_{24}N_2O_2$ |
| 1k | 7-n-BuO | H | COMe | H | H | 1 | i-PrOH | 174–176 | $C_{18}H_{26}N_2O_2$ |
| 1L | 7-n-PentO | H | COMe | H | H | 1 | EtOH | 190–191 | $C_{19}H_{28}N_2O_2$ |
| 1m | 7-n-HexO | H | COMe | H | H | 1 | EtOH | 197–199 | $C_{20}H_{30}N_2O_2$ |
| 1n | 7-PhCH$_2$O | H | COMe | H | H | 1 | i-PrOH | 183–184 | $C_{21}H_{24}N_2O_2$ |
| 1o | H | H | COMe | H | Me | 1 | i-PrOH | 190–191 | $C_{15}H_{20}N_2O$ |
| 1p | H | H | CHO | H | H | 1.1 | MeOH | 210–212 | $C_{13}H_{16}N_2O \cdot HCl$ |
| 1q | H | H | COEt | H | H | 1.5 | EtOH | 235–236 | $C_{15}H_{20}N_2O \cdot HCl$ |
| 1r | H | H | COBu—n | H | H | 1.5 | i-PrOH | 184–185 | $C_{17}H_{24}N_2O$ |
| 1s | H | H | CO$_2$Et | H | H | 1.5 | EtOH—Et$_2$O | 147–149 | $C_{15}H_{20}N_2O_2 \cdot HCl$ |
| 1t | H | H | CO$_2$Me | H | H | 1.5 | MeOH—Et$_2$O | 204–205 | $C_{14}H_{18}N_2O_2 \cdot HCL$ |
| 1u | H | H | H | H | H | 2 | MeOH | 304–306 | $C_{12}H_{16}N_2 \cdot 2HCl$ |
| 1v | H | H | Me | H | H | 5 | MeOH | 275–277 | $C_{13}H_{18}N_2 \cdot 2HCl$ |
| 1w | H | H | Et | H | H | 5 | MeOH | 273–275 | $C_{14}H_{20}N_2 \cdot 2HCl$ |
| 1x | H | H | Me | Me | H | 10 | MeOH—Et$_2$O | 243–245 | $C_{14}H_{20}N_2 \cdot 2HCl$ |
| 1y | H | H | COMe | H | Et | — | EtOAc—C$_6$H$_{12}$ | 150–151 | $C_{16}H_{22}N_2O$ |

[a] mol(s) NaBH$_3$CN/mol substrate

TABLE II

| No. | $Y_1$ | $Y_2$ | Example | Recrystn Solvent | Mp, °C. | Formula |
|---|---|---|---|---|---|---|
| 2a | H | H | 3 | Me$_2$CO | 208–209 | $C_{14}H_{16}N_2O$ |
| 2b | 6-F | H | 4 | EtOH | 209–210 | $C_{14}H_{15}FN_2O$ |
| 2c | 6-Cl | H | 4 | Me$_2$CO—CHCl$_3$ | 207–208 | $C_{14}H_{15}ClN_2O$ |
| 2d | 6-Br | H | 5 | EtOH | 210–211 | $C_{14}H_{15}BrN_2O$ |
| 2e | 8-F | H | 4 | EtOAc | 209–212 | $C_{14}H_{15}FN_2O$ |
| 2f | 5-Cl | 7-Cl | 4 | EtOH | 232–234 | $C_{14}H_{14}Cl_2N_2O$ |
| 2g | 6-Me | H | 5 | EtOH | 210–212 | $C_{15}H_{18}N_2O$ |
| 2h | 6-MeO | H | 6 | EtOH | 191–193 | $C_{15}H_{18}N_2O_2$ |
| 2i | 7-MeO | H | 7 | EtOH | 192–193 | $C_{15}H_{18}N_2O_2$ |
| 2j | 7-n-BuO | H | 8 | Me$_2$CO | 182–184 | $C_{18}H_{24}N_2O_2$ |
| 2k | 7-HO | H | 9 | i-PrOH | 245–246 | $C_{14}H_{16}N_2O_2$ |
| 2L | 7-EtO | H | 10 | i-PrOH | 184–186 | $C_{16}H_{20}N_2O_2$ |
| 2m | 7-n-PrO | H | 10 | i-PrOH | 172–174 | $C_{17}H_{22}N_2O_2$ |
| 2n | 7-n-PentO | H | 10 | i-PrOH | 181–182 | $C_{19}H_{26}N_2O_2$ |
| 2o | 7-n-HexO | H | 10 | i-PrOH | 177–178 | $C_{20}H_{28}N_2O_2$ |
| 2p | 7-PhCH$_2$O | H | 10 | i-PrOH | 187–189 | $C_{21}H_{22}N_2O_2$ |

TABLE III

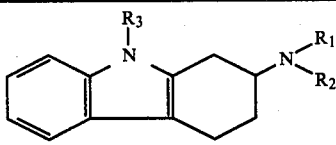

| No. | $R_1$ | $R_2$ | $R_3$ | Example | Recrystn Solvent | Mp, °C. | Formula |
|---|---|---|---|---|---|---|---|
| 3a | H | H | H | 11 | aq EtOH | ca. 290 d | $C_{12}H_{14}N_2 \cdot HCl$ |
| 3b | CHO | H | H | 12 | EtOH | 169–171 | $C_{13}H_{14}N_2O$ |
| 3c | COEt | H | H | 13 | EtOAc | 169–170 | $C_{15}H_{18}N_2O$ |
| 3d | COBu—n | H | H | 13 | EtOAc | 149–154 | $C_{17}H_{22}N_2O$ |
| 3e | $CO_2Et$ | H | H | 13 | EtOH | 164–165 | $C_{15}H_{18}N_2O_2$ |
| 3f | $CO_2Me$ | H | H | 13 | MeOH | 160–162 | $C_{14}H_{16}N_2O_2$ |
| 3g | $CO_2Et$ | Me | H | 14 | EtOH | 167–168 | $C_{16}H_{20}N_2O_2$ |
| 3h | COMe | Me | H | 15 | EtOH | 215–216 | $C_{15}H_{18}N_2O$ |
| 3i | Et | H | H | 16 | aq MeOH | 263–264 | $C_{14}H_{18}N_2 \cdot HCl$ |
| 3j | Me | H | H | 17 | aq EtOH | 252–253 | $C_{13}H_{16}N_2 \cdot HCl$ |
| 3k | Me | Me | H | 17 | EtOH—i-PrOH | 200–201 | $C_{14}H_{18}N_2 \cdot HCl$ |
| 3L | COMe | H | Me | 18 | EtOAc | 171–172 | $C_{15}H_{18}N_2O$ |

TABLE IV

Antagonism of Tetrabenazine-Induced Depression In Mice Orally at 1 Hour Post-Drug

| Compound No. | $ED_{50}$ (mg/kg) For Prevention of | |
|---|---|---|
|  | Ptosis | Exploratory Loss |
| 1a | 0.70 | 2.3 |
| 1b | 2.7 | 4.2 |
| 1c | 3.3 | 14.0 |
| 1d | 2.1 | 3.3 |
| 1e | 16 | 34 |
| 1f | 27 | 27 |
| 1g | 8.1 | 15.6 |
| 1h | 2.2 | 4.2 |
| 1i | 8.9 | 12.7 |
| 1j | 0.79 | 0.99 |
| 1k | 0.22 | 0.35 |
| 1L | 2.0 | 2.0 |
| 1m | 27 | 27 |
| 1n | 6.5 | 7.2 |
| 1o | 3.7 | 27 |
| 1p | 21 | 21 |
| 1q | 1.7 | 18 |
| 1r | 6.5 | 7.5 |
| 1s | 4.0 | 4.0 |
| 1t | 5.2 | 9.7 |
| 1u | 0.57 | 0.75 |
| 1v | 2.4 | 3.0 |
| 1w | 68 | 96 |
| 1x | 37 | 41 |
| 1y | 4.7 | 5.2 |
| 2a | 1.1 | 2.4 |
| 2b | 0.70 | 2.4 |
| 2c | 2.4 | 6.5 |
| 2d | 10.0 | 17.4 |
| 2e | 14.0 | 19.7 |
| 2f | 3.3 | 4.7 |
| 2g | 3.0 | 7.2 |
| 2h | 5.8 | 6.5 |
| 2i | 0.80 | 0.90 |
| 2j | 0.51 | 0.57 |
| 2k | >125 | >125 |
| 2L | 2 | 2 |
| 2m | 0.6 | 0.6 |
| 2n | 2.7 | 4.3 |
| 2o | 14.0 | 12.0 |
| 2p | 6.5 | 6.5 |
| 3a | 4.0 | 8.0 |
| 3b | 84 | >125 |
| 3c | 67 | >81 |
| 3d | >81 | >81 |
| 3e | 40 | >81 |
| 3f | >81 | >81 |
| 3g | 7.8 | 27 |
| 3h | >125 | >125 |
| 3i | 27 | 27 |
| 3j | 12 | 32 |
| 3k | 11.4 | 39 |
| 3L | 9.0 | 11.2 |
| amitriptyline | 1.2 | 2.6 |

What is claimed is:

1. A compound of the formula

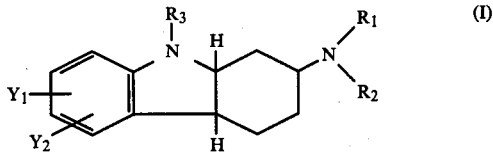

wherein
$R_1$ is hydrogen, methyl, ethyl, or

where R is hydrogen, or $C_1$–$C_4$ alkyl;
$R_2$ is hydrogen or methyl;
$R_3$ is hydrogen, methyl or ethyl;
$Y_1$ is hydrogen, fluorine, chlorine, bromine, hydroxy, methyl, benzyloxy or $C_1$–$C_6$ alkoxy;
$Y_2$ is hydrogen or chlorine; with the proviso that $Y_2$ can be chlorine only when $Y_1$ is chlorine;
or a pharmaceutically suitable salt thereof.

2. A compound of claim 1 wherein $R_2$ is hydrogen.

3. A compound of claim 1 wherein $Y_1$ is hydrogen, fluorine, chlorine or bromine or $C_1$–$C_4$ alkoxy.

4. A compound of claim 1 wherein $Y_2$ is hydrogen.

5. A compound of claim 1 wherein $R_2$ is hydrogen, $Y_1$ is hydrogen or $C_1$–$C_4$ alkoxy and $Y_2$ is hydrogen.

6. The compound of claim 1 which is cis-N-(1,3,4,4a,9,9a-hexahydro-2H-carbazol-2-yl)acetamide.

7. The compound of claim 1 which is cis-N-methyl-2,3,4,4a,9,9a-hexahydro-1H-carbazol-2-amine.

8. The compound of claim 1 which is cis-N-(1,3,4,4a,9,9a-hexahydro-2H-carbazol-2-yl)propanamide.

9. A pharmaceutical composition consisting essentially of a suitable pharmaceutical carrier and an effective antidepressant amount of a compound of claim 1.

10. A pharmaceutical composition consisting essentially of a suitable pharmaceutical carrier and an effective antidepressant amount of a compound of claim 2.

11. A pharmaceutical composition consisting essentially of a suitable pharmaceutical carrier and an effective antidepressant amount of a compound of claim 3.

12. A pharmaceutical composition consisting essentially of a suitable pharmaceutical carrier and an effective antidepressant amount of a compound of claim 4.

13. A pharmaceutical composition consisting essentially of a suitable pharmaceutical carrier and an effective antidepressant amount of a compound of claim 5.

14. A pharmaceutical composition consisting essentially of a suitable pharmaceutical carrier and an effective antidepressant amount of a compound of claim 6.

15. A pharmaceutical composition consisting essentially of a suitable pharmaceutical carrier and an effective antidepressant amount of a compound of claim 7.

16. A pharmaceutical composition consisting essentially of a suitable pharmaceutical carrier and an effective antidepressant amount of a compound of claim 8.

17. A method of alleviating depression in a mammal which comprises administering to the mammal an effective antidepressant amount of a compound of claim 1.

18. A method of alleviating depression in a mammal which comprises administering to the mammal an effective antidepressant amount of a compound of claim 2.

19. A method of alleviating depression in a mammal which comprises administering to the mammal an effective antidepressant amount of a compound of claim 3.

20. A method of alleviating depression in a mammal which comprises administering to the mammal an effective antidepressant amount of a compound of claim 4.

21. A method of alleviating depression in a mammal which comprises administering to the mammal an effective antidepressant amount of a compound of claim 5.

22. A method of alleviating depression in a mammal which comprises administering to the mammal an effective antidepressant amount of a compound of claim 6.

23. A method of alleviating depression in a mammal which comprises administering to the mammal an effective antidepressant amount of a compound of claim 7.

24. A method of alleviating depression in a mammal which comprises administering to the mammal an effective antidepressant amount of a compound of claim 8.

* * * * *